(12) United States Patent
Spector et al.

(10) Patent No.: US 8,084,428 B2
(45) Date of Patent: Dec. 27, 2011

(54) METHOD OF REPAIRING MENISCAL TEARS

(75) Inventors: Myron Spector, Brookline, MA (US); Peter Geistlich, Stansstad (CH); Lothar Schloesser, Darmstadt (DE); Roland Jakob, Moetier (CH); Jean-Francois Clemence, Gisikon (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 472 days.

(21) Appl. No.: 12/064,444

(22) PCT Filed: Sep. 1, 2006

(86) PCT No.: PCT/US2006/034329
§ 371 (c)(1),
(2), (4) Date: Aug. 11, 2008

(87) PCT Pub. No.: WO2007/028078
PCT Pub. Date: Mar. 8, 2007

(65) Prior Publication Data
US 2009/0186062 A1 Jul. 23, 2009

Related U.S. Application Data

(60) Provisional application No. 60/713,360, filed on Sep. 2, 2005.

(51) Int. Cl.
*A61K 38/39* (2006.01)
*A61P 19/02* (2006.01)

(52) U.S. Cl. .......... 514/17.1; 623/20.14; 623/908; 623/14.2; 514/7.6; 514/17.2

(58) Field of Classification Search .......... None
See application file for complete search history.

(56) References Cited

U.S. PATENT DOCUMENTS

| | | | |
|---|---|---|---|
| 5,206,023 A | 4/1993 | Hunziker | |
| 5,837,278 A | 11/1998 | Geistlich et al. | |
| 6,221,109 B1 | 4/2001 | Geistlich et al. | |
| 6,352,558 B1 | 3/2002 | Spector | |
| 6,444,222 B1 | 9/2002 | Asculai et al. | |
| 6,514,514 B1 * | 2/2003 | Atkinson et al. | 424/423 |
| 6,713,085 B2 | 3/2004 | Geistlich et al. | |
| 6,866,668 B2 | 3/2005 | Giannetti et al. | |
| 2003/0039695 A1 * | 2/2003 | Geistlich et al. | 424/484 |
| 2003/0095994 A1 | 5/2003 | Geistlich et al. | |
| 2004/0013712 A1 | 1/2004 | Parma | |
| 2004/0059416 A1 * | 3/2004 | Murray et al. | 623/13.15 |
| 2004/0170664 A1 | 9/2004 | Spector et al. | |
| 2005/0234549 A1 * | 10/2005 | Kladakis et al. | 623/14.12 |

FOREIGN PATENT DOCUMENTS

| | | |
|---|---|---|
| EP | 1084720 B1 | 3/2005 |
| EP | 1252903 B1 | 11/2006 |
| GB | 2366736 A | 3/2002 |
| JP | 2003160506 | 6/2003 |
| JP | 2003180815 | 7/2003 |
| WO | 0009179 A2 | 2/2000 |
| WO | 0209790 A1 | 2/2002 |
| WO | 02083878 A1 | 10/2002 |

OTHER PUBLICATIONS

European supplementary Search Reported dated Jun. 17, 2011 in EP apln. No. 06802853.9, 8 pages.
Japanese Office Action dated Jul. 19, 2011 (partial translation) in JP apln. No. 529334/2008, 4 pages.

* cited by examiner

*Primary Examiner* — Daniel C Gamett

(74) *Attorney, Agent, or Firm* — Rothwell, Figg, Ernst & Manbeck, P.C.

(57) ABSTRACT

A method of repairing a meniscal tear of a subject includes providing a sheet of collagen membrane material having on one side thereof a smooth barrier face which inhibits cell adhesion thereon and inhibits passage of cells therethrough. The sheet has a fibrous face opposite the smooth barrier face, the fibrous face allowing cell growth thereon. The collagen is predominantly collagen I. The sheet of collagen membrane material is fixed over a meniscal tear so that the fibrous face is oriented toward the meniscal tear.

20 Claims, 1 Drawing Sheet

METHOD OF REPAIRING MENISCAL TEARS

CROSS-REFERENCE TO RELATED APPLICATIONS

This application is a 35 U.S.C. §371 National Phase Entry Application of PCT/US2006/034329, filed Sep. 1, 2006, and claims the benefit of provisional U.S. Provisional Application Ser. No. 60/713,360, filed Sep. 2, 2005.

BACKGROUND OF THE INVENTION

1. Field of the Invention

The present invention relates to the field of repairing meniscal tears.

2. Description of the Background Art

Meniscal tears in a joint of a subject, e.g., in a knee, are frequent injuries. In the past, a torn meniscus often was partially or completely removed. In recent years, techniques have been developed for repairing meniscal tears, including the use of arthroscopically placed tacks or suturing the torn edges.

There remains a need in the art for new methods of repairing meniscal tears.

SUMMARY OF THE INVENTION

In accordance with the present invention, a method of repairing a meniscal tear of a subject comprises providing a sheet of collagen membrane material, the sheet having on one side thereof a smooth barrier face which inhibits cell adhesion thereon and inhibits passage of cells therethrough, the sheet having a fibrous face opposite the smooth barrier face, the fibrous face allowing cell growth thereon, the collagen of said sheet being predominantly collagen I. The sheet of collagen membrane material is fixed over the meniscal tear so that the fibrous face is oriented toward the meniscal tear.

DETAILED DESCRIPTION OF THE INVENTION

Figure 1:
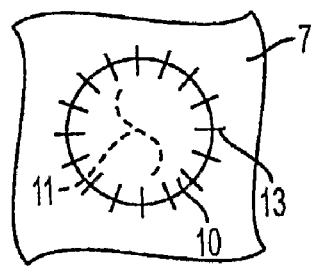
FIG. 1 is a side elevation schematic view showing covering of one side of a meniscus tear in accordance with one embodiment of the invention.

Cells that contribute to the reparative process of a torn meniscus are from adjacent synovial tissue. In addition to contributing to the reparative process in a torn meniscus, synovial cells have the capability to degrade connective tissues and to contract. For example, synovial tissue can break down typical collagen I scaffolds.

It has surprisingly been discovered that the predominantly collagen I membrane of the present invention is able to maintain its integrity when in contact with synovial tissue, and also serve as a scaffold into which synovial cells can migrate to facilitate healing of a meniscal tear.

A sheet of collagen membrane material utilized in accordance with the present invention has on one side thereof a smooth barrier face which inhibits cell adhesion thereon and inhibits passage of cells therethrough. The collagen sheet has a fibrous face opposite the barrier face, the fibrous face allowing cell growth thereon.

As noted above, the collagen of a membrane utilized in accordance with the present invention is predominantly collagen I, i.e., greater than 50% collagen I by weight. In preferred embodiments, the collagen I content of a membrane sheet utilized in accordance with the present invention may be greater than 60% by weight, greater than 70% by weight, greater than 80% by weight or greater than 90% by weight. In accordance with one embodiment, the collagen of a membrane sheet utilized in accordance with the present invention is approximately 95% by weight collagen I. The collagen of such a membrane may comprise approximately 5% by weight collagen III.

In preferred embodiments, the collagen utilized in the present invention is of porcine or bovine origin. In particularly preferred embodiments, the sheet of collagen material utilized in the present invention is formed from a naturally occurring membrane of porcine or bovine origin, preferably from calves or piglets. A preferred source is naturally occurring single-layered sheets of peritoneum membrane, most preferably from piglets. Peritoneum membranes from young pigs aged 6-7 weeks old (weighing 60-80 kg) are especially preferred. One such material is described in U.S. Pat. No. 5,837,278, incorporated herein by reference.

The dry thickness of a membrane for use in the present invention may be between about 0.1-5.0 mm, preferably between about 0.1-1.0 mm, or about 0.5 mm, but can be influenced by swelling of the material when exposed to moisture.

A sheet of collagen membrane material utilized in accordance with the present invention is fixed over a meniscal tear so that the fibrous face of the membrane is oriented toward the meniscal tear. The sheet may be fixed by any suitable means, including sutures, a physiologically acceptable adhesive (e.g., fibrin glue), or a combination thereof. The membrane preferably completely covers at least one side of the tear, and the fibrous face preferably contacts the tear.

A sheet of collagen membrane material utilized in accordance with the present invention may be fixed over one side of a meniscal tear, or additionally a second sheet of collagen membrane material may be fixed on an opposite side of a meniscal tear, also with the fibrous face oriented toward the tear, so that the meniscal tear is sandwiched between two sheets of collagen membrane material.

In accordance with one embodiment, when a single sheet of collagen membrane material is fixed over one side of a meniscal tear, the fibrous face of the membrane is contact with synovial fluid in the subject which migrates through the tear into the fibrous face.

One suitable membrane for use in accordance with the present invention is ChondroGide®, manufactured by Ed. Geistlich Soehne AG für Chemische Industrie, the assignee of the present invention.

Figure 2:
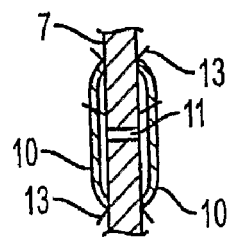
FIG. 2 is a schematic sectional view showing both sides of a meniscal tear treated according to another embodiment.

As shown in FIG. 1, the membrane material 10 may be fixed over a meniscus tear 11 in meniscus 7 by adhesive or sutures 13 attached to meniscus 7. In accordance with one embodiment of the invention as shown in FIG. 2, during surgery in which a meniscus tear 11 in meniscus 7 is treated, separate sheets of collagen membrane material 10 are fixed over the meniscus tear 11 so as to cover the tear on opposite sides thereof, with the tear being sandwiched between the membrane material 10, to thereby provide a barrier against ingrowth of connective tissue into meniscus tissue 7 following the surgery. The sheet of collagen membrane material preferably is fixed over the area to be treated, for example, by adhesive bonding of the sheet, utilizing an organic glue, such as fibrin glue, or by sutures 13, or a combination thereof, or any other suitable method.

Figure 3:
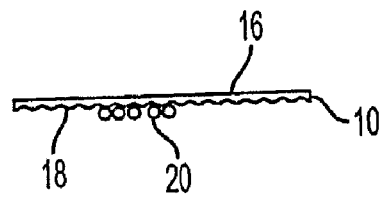
FIG. 3 is a side elevation schematic view showing a collagen membrane for use in accordance with the present invention with adjacent synovial cells.

As noted above, the collagen membrane material 10 is comprised of at least one barrier layer having at least one smooth face 16 so as to inhibit cell adhesion thereon and act as a barrier to prevent passage of cells therethrough. See FIG. 3. The membrane 10 further has a fibrous face 18 opposite the smooth face 16, the fibrous face allowing cell growth thereon. Synovial cells 20 may contact the fibrous face 18 and migrate into the membrane to assist in healing of the tear.

In one embodiment, a collagen membrane material is utilized, wherein the membrane and/or the fibrous face are impregnated with chondrocytes, synovial fibroblast-like cells, mesenchymal stem cells, one or more glycosaminoglycans, and/or one or more growth factors. Examples of suitable glycosaminoglycans include hyaluronic acid, chondroitin 6-sulphate, keratin sulphate, dermatan sulphate or the like. Suitable growth factors include, but are not limited to, those which are described as follows. Transforming growth factor-beta (TGF-beta) increases the proteoglycan synthesis of fibrochondrocytes isolated from different sections of the menisci in a dose dependent manner. Human platelet-derived growth factor (PDGF-AB), hepatocyte growth factor (HGF) and bone morphogenic protein-2 (BMP-2) increase DNA synthesis in meniscal cells. In addition, BMP-2, insulin-like growth factor-1 (IGF-1), and epidermal growth factor (EGF) stimulate migration of bovine fibrochondrocytes from the different parts of the menisci. Also suitable is osteogenic protein-1 (OP-1).

The present invention provides a smooth barrier face 16 in membrane 10 which protects the surgical site from ingrowth of unwanted cells during the healing process, and a fibrous face 18 for promoting growth of reparative cells adjacent the tear. The collagen membrane material 10 is gradually resorbed into the patient's body, avoiding any necessity of having to surgically remove the membrane after healing.

While the invention has been described in detail, it is not intended that the description and accompanying drawings be interpreted in a limiting sense.

The invention is further illustrated by the following example, which is not intended to be limiting.

Example 1

Application of ChondroGide® Membrane for the Treatment of Meniscal Tears

In Vitro Experiments

A ChondroGide® membrane may be applied to a torn meniscus to facilitate its repair. The cells that contribute to the reparative process are from the adjacent synovial tissue. In addition to contributing to the reparative process in a torn meniscus, these synovial cells have the capability to degrade connective tissues and to contract. The ChondroGide® membrane will: (1) guide synovial cells to the tear in the meniscus by serving as a scaffold on which the cells can migrate, and (2) contain the cells in the defect during the reparative process. The ChondroGide® membrane is able to maintain its integrity when in contact with synovial tissue, and also serve as a scaffold into which the synovial cells can migrate. In vitro data demonstrates that, while synovial tissue can break down bovine type I collagen scaffolds, it does not degrade ChondroGide®, and the ChondroGide® membrane retains its size and shape despite the contraction of synovium. Moreover, cells from synovium can migrate into ChondroGide®.

In the experimental work, samples of caprine synovium, 8 mm in diameter, were placed on ChondroGide® membranes and on a typical bovine type I collagen scaffold. After 7 days in vitro, the synovium specimens cultured on the ChondroGide® and directly on the tissue culture dish contracted to about ½ the original size. Of importance was the finding that the ChondroGide® retained its original size and shape, and was not degraded by the synovium. As a control, similar synovial tissue samples were cultured on bovine type I collagen scaffolds. The synovial samples in these cultures also contracted. The data show that after only 24 hours the synovial cells digested the prior art collagen I scaffold, and as a result some of the synovium samples were displaced from the scaffold. A similar degradation of the bovine type I collagen scaffold was seen after 48 hours in culture.

Histology demonstrated that cells from synovium can migrate into ChondroGide® membranes. After 21 days in culture, cells from the synovial tissue samples migrated from the synovium into the ChondroGide®. Synovial cells could be found throughout the ChondroGide® membrane.

The invention claimed is:

1. A method of repairing a meniscal tear of a subject comprising fixing a first sheet of collagen membrane material over a meniscal tear and further comprising fixing a second sheet of said collagen membrane material on an opposite side of said meniscal tear so that said meniscal tear is sandwiched between both sheets of said membrane material, wherein said sheets of collagen membrane are predominantly collagen I, wherein said sheets of collagen membrane have on one side thereof a smooth barrier face which inhibits cell adhesion thereon and inhibits passage of cells therethrough, and have a fibrous face opposite said smooth barrier face which allows cell growth thereon, and wherein the fibrous faces of said sheets of collagen membrane are oriented toward said meniscal tear.

2. The method of claim 1 wherein said fibrous faces of said sheets of collagen membrane material are in contact with synovial fluid in said subject.

3. The method of claim 1 wherein said sheets of collagen membrane material are fixed over said meniscal tear with sutures, physiologically acceptable adhesive or a combination thereof.

4. The method of claim 3 wherein said adhesive is fibrin glue.

5. The method of claim 1 wherein the collagen of said membrane material is greater than about 60% by weight collagen I.

6. The method of claim 1 wherein said collagen of said membrane material is greater than about 70% by weight collagen I.

7. The method of claim 1 wherein said collagen of said membrane material is greater than about 80% by weight collagen I.

8. The method of claim 1 wherein said collagen of said membrane material is greater than about 90% by weight collagen I.

9. The method of claim 1 wherein said collagen membrane material is porcine or bovine.

10. The method of claim 9 wherein said sheets of collagen membrane material are derived from peritoneum membrane.

11. The method of claim 10 wherein said peritoneum membrane is porcine.

12. The method of claim 11 wherein said collagen of said membrane material is about 95% collagen I.

13. The method of claim 12 wherein said collagen of said membrane material is about 5% collagen III.

14. The method of claim 11 wherein said collagen of said membrane material is about 95% collagen I and about 5% collagen II.

15. The method of claim 1 wherein said sheets of collagen membrane material have a dry thickness within a range of about 0.1-1 mm.

16. The method of claim 1 wherein the smooth barrier faces, the fibrous faces or both of said sheets of collagen membrane material, are impregnated with at least one of chondrocytes, fibroblast-like cells, mesenchymal stem cells, at least one glycosaminoglycan, at least one growth factor or a mixture thereof.

17. The method of claim 16 wherein the glycosaminoglycan is hyaluronic acid, chondroitin 6-sulphate, keratin sulphate or dermatan sulphate.

18. The method of claim 16 wherein said at least one growth factor is transforming growth factor beta, human platelet-derived growth factor, hepatocyte growth factor, bone morphogenic protein-2, insulin-like growth factor-1, epidermal growth factor, osteogenic protein-1, or a mixture thereof.

19. The method of claim 18 wherein said growth factor is hepatocyte growth factor, epidermal growth factor, or a mixture thereof.

20. The method of claim 16 wherein the smooth barrier faces, the fibrous faces or both of said sheets of collagen membrane material are impregnated with fibroblast-like cells.

\* \* \* \* \*